US009410932B2

(12) United States Patent
Kim et al.

(10) Patent No.: US 9,410,932 B2
(45) Date of Patent: Aug. 9, 2016

(54) METHOD OF MEASURING DISSOLVED METHANE IN SEAWATER

(71) Applicant: KOREA INSTITUTE OF GEOSCIENCE AND MINERAL RESOURCES, Daejeon (KR)

(72) Inventors: Ji-Hoon Kim, Daejeon (KR); Jiyoung Choi, Daejeon (KR); Sungkyoung Hong, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 32 days.

(21) Appl. No.: 14/724,647

(22) Filed: May 28, 2015

(65) Prior Publication Data

US 2015/0355155 A1    Dec. 10, 2015

(30) Foreign Application Priority Data

Jun. 9, 2014   (KR) .................. 10-2014-0069154

(51) Int. Cl.
| | |
|---|---|
| *G01N 33/18* | (2006.01) |
| *G01N 30/04* | (2006.01) |
| *G01N 30/00* | (2006.01) |
| *G01N 30/72* | (2006.01) |

(Continued)

(52) U.S. Cl.
CPC ............ *G01N 33/1826* (2013.01); *B01D 61/36* (2013.01); *G01N 1/10* (2013.01); *G01N 1/28* (2013.01); *G01N 7/14* (2013.01); *G01N 21/61* (2013.01); *G01N 30/00* (2013.01); *G01N 30/04* (2013.01); *G01N 30/72* (2013.01); *G01N 30/88* (2013.01); *Y10T 436/214* (2015.01)

(58) Field of Classification Search
CPC ... G01N 33/1826; G01N 30/00; G01N 30/04; G01N 30/88; G01N 21/61; G01N 7/14; G01N 1/10; G01N 1/28; G01N 30/72; Y10T 436/214; B01D 61/36
See application file for complete search history.

(56) References Cited

U.S. PATENT DOCUMENTS

2009/0084976 A1* 4/2009 Camilli ................... H01J 49/24
250/397

OTHER PUBLICATIONS

Schluter et al, "Application of Membrane Inlet Mass Spectrometry for Online and In Situ Analysis of Methane in Aquatic Environments", Journal of the American Society for Mass Spectrometry, vol. 19, Issue 10, Oct. 2008, pp. 1395-1402.*

(Continued)

*Primary Examiner* — Jennifer Wecker
(74) *Attorney, Agent, or Firm* — Alleman Hall McCoy Russell & Tuttle LLP

(57) ABSTRACT

Provided is a method of measuring dissolved methane in seawater, including: a) injecting a sample into a vacuum container containing a cadmium chloride solution injected thereinto and refrigerating the vacuum container; b) shaking the vacuum container, and achieving temperature equilibrium with an ambient temperature; c) separating the dissolved methane from residue by passing the sample in the vacuum container through a methane separator; and d) analyzing the separated dissolved methane by a mass spectrometer. According to the method of measuring dissolved methane in seawater of the present invention, a recovery rate of dissolved methane may be maximally increased to improve an analysis rate accordingly, and an analysis of dissolved methane may be conducted even with a small amount of sample, and in addition to the measurement of the dissolved methane, a sulfur isotope analysis may be simultaneously conducted by using a sample from which the dissolved methane is extracted.

5 Claims, 2 Drawing Sheets

(51) Int. Cl.
     *B01D 61/36*  (2006.01)
     *G01N 21/61*  (2006.01)
     *G01N 7/14*   (2006.01)
     *G01N 1/10*   (2006.01)
     *G01N 30/88*  (2006.01)
     *G01N 1/28*   (2006.01)

(56) References Cited

OTHER PUBLICATIONS

Hong, S., "Possibility of Increase in Atmospheric Greenhouse Gas and Climate Change," Chemical Industry and Technology, vol. 13, No. 4, Apr. 1995, 9 pages. (Submitted with translation of abstract).

An, S. et al., "An Improved Chromatographic Method to Measure Nitrogen, Oxygen, Argon and Methane in Gas or Liquid Samples," Marine Chemistry, vol. 59, No. 1-2, Dec. 1997, 8 pages.

Choi, G. et al., "Studies of Long-Term Variability of Methane in the Moo-Ahn Observatory Site in Korea," Jour. Korean Earth Science Society, vol. 23, No. 3, Feb. 2002, 14 pages.

An, S. et al., "Dissolved Methane Measurements in Seawater and Sediment Porewater Using Membrane Inlet Mass Spectrometer (MIMS) System," The Sea—Journal of the Korean Society of Oceanography, vol. 12, No. 3, Aug. 2007, 7 pages.

Korean Intellectual Property Office, Office Action Issued in Korean Patent Application No. 10-2014-0069154, Aug. 4, 2014, 8 pages.

* cited by examiner

METHOD OF MEASURING DISSOLVED METHANE IN SEAWATER

CROSS-REFERENCE TO RELATED APPLICATIONS

This application claims priority under 35 U.S.C. §119 to Korean Patent Application No. 10-2014-0069154, filed on Jun. 9, 2014, in the Korean Intellectual Property Office, the disclosure of which is incorporated herein by reference in its entirety.

TECHNICAL FIELD

The following disclosure relates to a method of measuring concentration of dissolved methane contained in seawater, and more specifically, to a method of measuring concentration of dissolved methane contained in seawater, capable of maximally increasing a recovery rate of dissolved methane to improve an analysis rate accordingly, which is unlike existing sampling methods, and conducting an analysis of dissolved methane even with a small amount of sample, and simultaneously conducting a sulfur isotope analysis in dissolved sulfurated water in addition to the measurement of the dissolved methane.

BACKGROUND

Methane is known as a main cause of greenhouse effect and is 20 times more lethal than carbon dioxide in the same amount. However, simultaneously, methane has been in the limelight as one of the most important energy resources. In particular, methane is a main component of natural gas, and is available in large quantities, and as a result, is preferably desired to be used as fuel. However, since methane is present in a gaseous state at room temperature-atmospheric pressure, it is difficult to transport and store methane, and a methane reservoir is considerably overlapped with an oil reservoir, such that usage depends heavily on imports.

Methane is generally present in the gaseous state as described above; however, may be stored in a form of methane hydrate in the ocean's and earth's crust. The methane hydrate is a solid material containing methane molecules in a crystal structure of water molecules under conditions of low temperature and high pressure, and is known to be buried in quantity in the East Sea of Korea, and The Government Development Project Group found about 600 million tons of methane hydrates under the sea at about 100 km south from Ulleung Island in June 2005. This amount corresponds to domestic consumption of natural gas for about thirty years.

Development and utilization of the metal hydrate as new energy resources are currently being planned as a national project. However, since the methane hydrate is present as a solid in deep sea, it is difficult to apply existing methods of mining the natural gas. Therefore, development of a new mining technology has been demanded.

In addition, accompanying with the development of the mining technology, the methane hydrate is partially decomposed and melted in the seawater, such that a technology of measuring an amount of dissolved methane present in the seawater has also been demanded. In general, the measurement of the dissolved methane is performed by the following two steps:

A first step is to extract methane gas in a dissolved state as a methane gas in a gaseous state, and a second step is to quantify the extracted methane gas. Extraction of the gas in the dissolved state is mainly performed by using a headspace, by using purge-trapping, by using an equilibrator, and the like. The extracted methane is quantified by gas chromatography equipped with a flame ionization detector (FID) and a photo-acoustic infrared detector. These methods are advantageous in that since methane in air has significantly low concentration, there is a small possibility in polluting a sample, and detectors used for quantification are possible to measure the low concentration, and therefore, a measurement error is generally small. However, the methods of using the headspace or purge-trapping have problems in that it takes a long time for processing the sample, and accuracy in measuring the concentration is decreased in a step of extracting the dissolved gas (An and Joye, 1997). In addition, an amount of the sample required for the measurement is relatively large as 50 to 600 ml or more, which makes it difficult to repeat experiments.

RELATED ART DOCUMENT (Non-Patent Document 1) Gyu Hoon, Choi, et al., 2002; Study of Long-Periodic Concentration Change Characteristics of Methane based on Muan-Gun Chonnam-Province, Korea; Journal of the Korean Earth Science Society, 23(3): 280-293.

(Non-Patent Document 2) Seong Gil, Hong, 1995; Possibility of Increase in Atmospheric Greenhouse Gas and Climate Change; Chemical Engineering Technology, 13(4): 354-360.

SUMMARY

An embodiment of the present invention is directed to providing a method of measuring dissolved methane in seawater capable of maximally increasing a recovery rate of dissolved methane to improve an analysis rate accordingly, and conducting an analysis of dissolved methane even with a small amount of sample to solve the above-described problems.

Another embodiment of the present invention is directed to providing a method of measuring dissolved methane in seawater capable of simultaneously conducting a sulfur isotope analysis in dissolved sulfurated water by using a sample from which the dissolved methane is extracted, in addition to the measurement of the dissolved methane.

In one general aspect, there is provided a method of measuring dissolved methane in seawater.

The method of measuring dissolved methane in seawater includes:

a) injecting a sample into a vacuum container containing a cadmium chloride solution injected thereinto and refrigerating the vacuum container;

b) shaking the vacuum container, and achieving temperature equilibrium with an ambient temperature;

c) separating the dissolved methane from residue by passing the sample in the vacuum container through a methane separator; and d) analyzing the separated dissolved methane by a mass spectrometer.

The method may further include: e) filtering a precipitated material from the sample from which the dissolved methane is removed and analyzing a sulfur isotope in dissolved sulfurated water.

The injecting of the sample into the vacuum container a) may include:

a1) injecting the cadmium chloride solution into the vacuum container and sealing the vacuum container;

a2) making an inner part of the vacuum container to be in a vacuum state by using a vacuum pump; and a3) injecting the sample into the vacuum container and refrigerating the vacuum container at 0 to 10° C.

The methane separator may include:

a vacuum housing connected to the vacuum container, a mass spectrometer, and a residue processor;

a silicone tube positioned in the vacuum housing, allowing the sample to pass through, and separating methane from the sample;

a stainless steel pipe supplying the sample to the silicone tube; and a vacuum pump maintaining an inner part of the vacuum housing to be in a vacuum state.

In the methane separator, the methane may be separated by injecting the sample into the vacuum housing and then inserting the silicone tube attached to one end of the stainless steel pipe into the sample.

The cadmium chloride solution may be injected in an amount of 1 to 40 parts by weight based on 100 parts by weight of the sample.

DETAILED DESCRIPTION OF MAIN ELEMENTS

Figure 1:
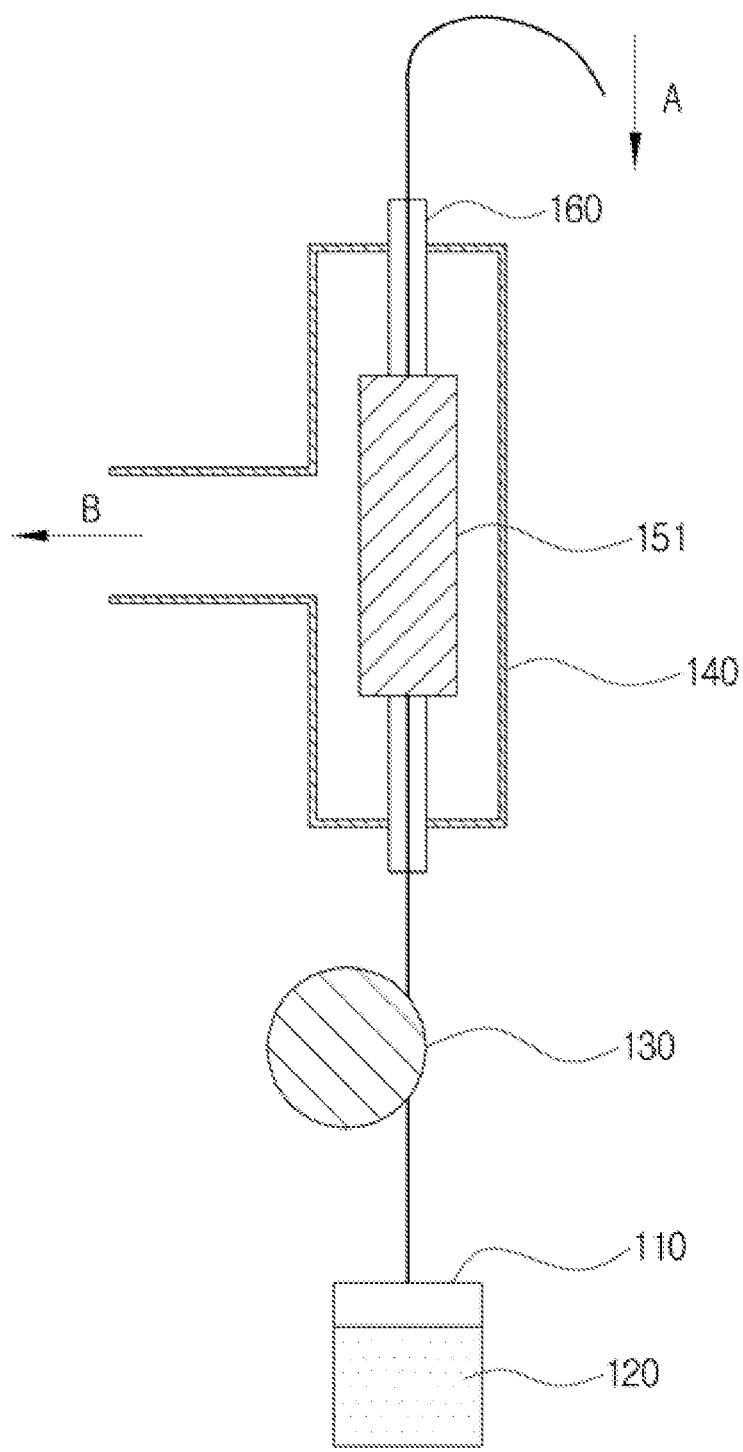
FIGS. 1 and 2 illustrate methane separators according to an exemplary embodiment of the present invention.

110: container
111: stopper
120: sample
130: peristaltic pump
140: vacuum housing
150: detector
151: silicone tube
152: shrink tube
160: stainless steel pipe
170: micro control device
180: shrink piston

DETAILED DESCRIPTION OF EMBODIMENTS

Hereinafter, the present invention will be described in more detail according to specific exemplary embodiments and Examples with reference to the accompanying drawings. Meanwhile, the following exemplary embodiments and Examples are provided as a reference for explaining the present invention in detail, and therefore, the present invention is not limited thereto, but may be implemented in various ways.

Unless defined otherwise, all technical and scientific terms used herein have the same meanings generally understood by those skilled in the art to which the present invention pertains. Terms used in the specification of the present invention are to effectively describe specific exemplary embodiments, but are not intended to limit the present invention.

In addition, the drawings to be described below are provided by way of example so that the idea of the present invention can be sufficiently transferred to those skilled in the art to which the present invention pertains. Therefore, the present invention may be implemented in many different forms, without being limited to the drawings to be described below. The drawings may be exaggerated in order to specify the spirit of the present invention. Further, like reference numerals denote like components throughout the specification.

It is intended that singular forms used in the appended specification and claims include plural forms unless otherwise indicated in the context.

In a method of measuring dissolved methane according to the present invention, different extraction systems depending on forms (liquid, solid) of the sample may be used. The method of measuring dissolved methane has advantages in that a recovery rate of the dissolved methane may be maximally increased to improve an analysis rate accordingly, and an analysis of dissolved methane may be conducted even with a small amount of sample.

The method of measuring dissolved methane in seawater according to the present invention may include:

injecting a sample into a vacuum container containing a cadmium chloride solution injected thereinto and refrigerating the vacuum container;

shaking the vacuum container, and achieving temperature equilibrium with an ambient temperature;

separating the dissolved methane from residue by passing the sample in the vacuum container through a methane separator; and analyzing the separated dissolved methane by a mass spectrometer.

In addition, a) the injecting of the sample into the vacuum container may include:

a1) injecting the cadmium chloride solution into the vacuum container and sealing the vacuum container;

a2) making an inner part of the vacuum container to be in a vacuum state by using a vacuum pump; and a3) injecting the sample into the vacuum container and refrigerating the vacuum container at 0 to 10° C.

The container is not limited in view of a size and a material, but is preferably an opaque glass material which does not pass through a solar light, and the like, in order to inhibit an activity of microorganisms capable of generating methane, such as bacteria, archaebacteria, and the like. In particular, since the bacteria generating the methane generates the methane by an energy metabolism in an anaerobic condition, it is preferable to suppress this condition.

The cadmium chloride according to the present invention is a material inhibiting the activity of the microorganism, and having a colorless and transparent lamina crystal form. In general, examples of a cadmium compound include cadmium oxide (CdO), cadmium nitrate ($Cd(NO_3)_2 \cdot 4H_2O$), cadmium sulfate ($CdSO_4 \cdot 8/3H_2O$), cadmium stearate ($Cd(C_{18}H_{35}O_2)_2$), cadmium sulfide (CdS), and the like, in addition to cadmium chloride. However, since cadmium oxide, cadmium stearate, cadmium sulfide, and the like, are insoluble in water, they are not suitable for being used in the present invention, and therefore, cadmium chloride is preferably used.

In addition, the cadmium chloride solution according to the present invention reacts with dissolved hydrogen sulfide ions ($HS^-$) contained in the sample to precipitate cadmium sulfide (CdS). In existing methods of measuring the dissolved methane in the seawater, mercury chloride is used; however, the mercury chloride itself has high toxicity and does not have any effect except for inhibiting the activity of the microorganisms. The present invention has advantages in that by substituting mercury chloride with cadmium chloride, a microbial activity inhibitory effect which is the existing purpose of adding the mercury chloride may be expressed in the same level, and by precipitating dissolved hydrogen sulfide ions as the cadmium sulfide, an analysis of sulfur isotope in addition to the analysis of the dissolved methane may be conducted.

The cadmium chloride solution according to the present invention is preferably added in an amount of 1 to 40 parts by weight based on 100 parts by weight of a sample for measurement. When an amount of the added cadmium chloride solution is less than 1 part by weight, it is difficult to properly express an effect in which microorganisms are inhibited and an effect in which cadmium sulfide is precipitated, and when an amount of the added cadmium chloride solution is more than 40 parts by weight, an amount of the sample to be used is small, such that an amount of cadmium sulfide precipitation is also small, and therefore, caution at the time of pretreatment is significantly required.

After the cadmium chloride solution is injected into the container, the container is sealed to block contact between the sample and air. The sealing method is not limited in the present invention, and may proceed by generally performed methods in the art.

After the container into which the cadmium chloride solution is injected is sealed, an inner part of the container may be in a vacuum state by using a vacuum pump as described in step a2) above. The reason is to remove the air present in the container to thereby prevent a composition change of the sample, wherein the vacuum state may be formed by generally performed vacuum forming methods in addition to the vacuum pump, and the present invention is not limited thereto.

Then, the sample is injected into the container in a vacuum state and refrigerated at 0 to 10° C. to prevent a change of the sample.

In the present invention, the sample may be a sediment core collected from seawater, methane hydrate layer, mud flat, or the like. Here, the sample may be collected by using water sampler or placer dredger capable of collecting the sample according to a depth of water. In addition, in the present invention, a method of injecting the sample into the container is not limited, and for example, a sample in a liquid state or a solid state may be injected by using a quantitative syringe, and the like.

The container into which the sample is injected may be refrigerated in a constant temperature water bath, and the like. Here, a storage temperature may be 0 to 10° C., and a storage time may be 24 hours or more, preferably, 24 to 72 hours.

Then, after the container is shaken as described in step b), a temperature in the container is equilibrated with an ambient temperature. In the present invention, the sample in the container may be more uniformly positioned by shaking the container as described above. In addition, the temperature may be room temperature, more specifically, 20 to 30° C., and it is preferred that the sample is stored in the constant temperature water bath for 48 hours or more.

After the constant temperature process is finished, the sample in the container may be passed through the methane separator to separate the dissolved methane and the residue.

In the present invention, the methane separator may include a vacuum housing connected to the vacuum container, a mass spectrometer, and a residue processor; a silicone tube positioned in the vacuum housing, allowing the sample to pass through, and separating methane from the sample; a stainless steel pipe supplying the sample to the silicone tube; and a vacuum pump maintaining an inner part of the vacuum housing to be in a vacuum state.

Hereinafter, the above-description is described in more detail with reference to FIGS. 1 and 2. First, FIG. 1 illustrates a methane separator when a sample is liquid such as seawater, and the like, wherein a container 110 into which the sample 120 is injected is connected to a vacuum housing 140 through a stainless steel pipe 160. A silicone tube 151 connected to the stainless steel pipe 160 may be positioned in the vacuum housing 140.

The sample in the container is introduced into the stainless steel pipe through a peristaltic pump, and the stainless steel pipe is communicated with the silicone tube in the vacuum housing in a vacuum state, and gas may be selectively penetrated into the silicone tube, such that when a liquid sample passes through the silicone tube, dissolved gas is extracted through a silicone membrane. In addition, residue from which the dissolved gas is extracted proceeds in an A direction and discharged to the outside of the vacuum housing through a residue processor (not shown). Further, the dissolved gas separated from the sample by the silicone tube may be introduced into gas chromatography in a B direction, and components thereof may be analyzed. Meanwhile, the dissolved gas may be further subjected to a liquid nitrogen trap process (not shown) before being introduced into a mass spectrometer in order to remove moisture.

Figure 2:
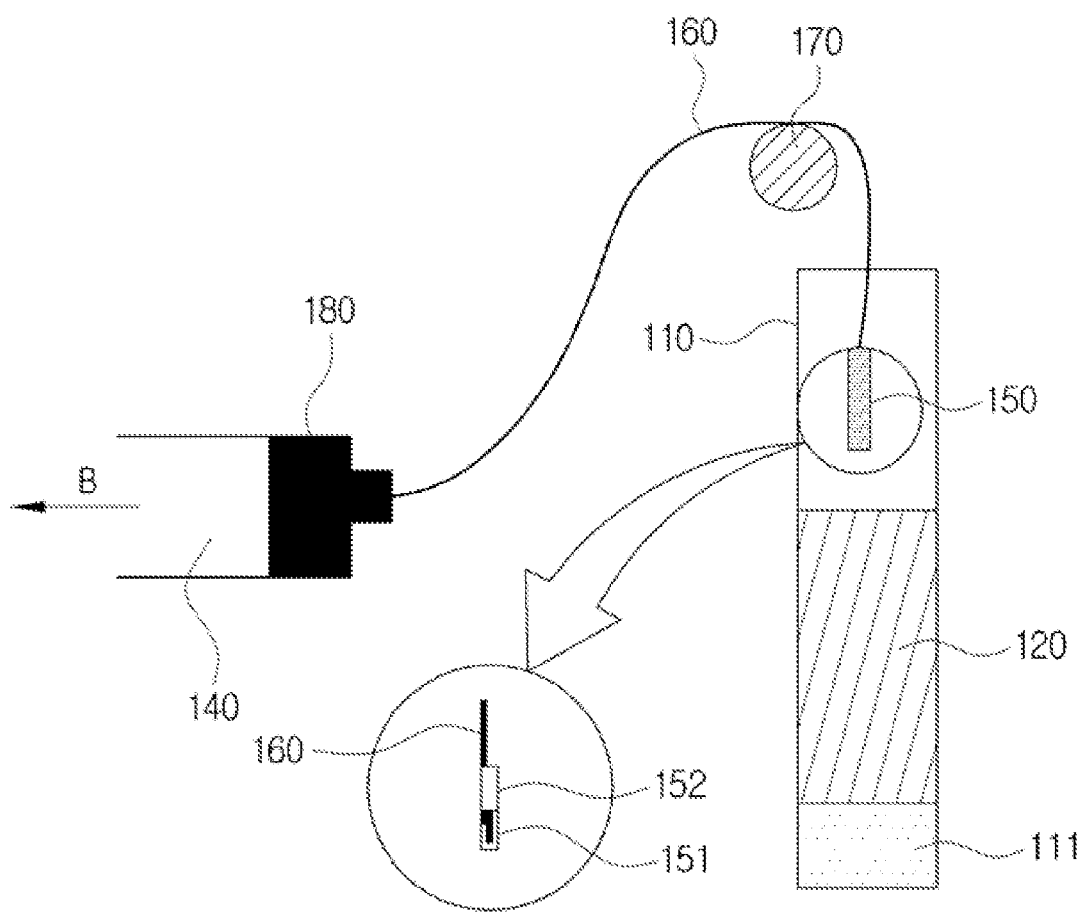

FIG. 2 illustrates a methane separator when a sample is solid such as a sediment, and the like, wherein fundamental analysis method and gas separation principle are the same as FIG. 1. Meanwhile, in a case of the sediment, pore water is present a core, and gases such as methane, and the like, are melted in the pore water, such that when a size of the silicone tube is large, the tube may be blocked due to the sediment. Therefore, a detector 150 including a minimum sized silicone tube may be directly inserted into the sediment and the dissolved gas in the pore water may be extracted by the silicone tube.

The detector may be directly connected to the vacuum housing 140 in a vacuum state through the stainless steel pipe 160, and the silicone tube 151 may be attached to one end of the stainless steel pipe, and folded in half and sealed. That is, an inner side of the silicone tube is directly connected to the stainless steel pipe, thereby maintaining that the gas in the pore water is capable of being easily extracted in the vacuum housing in which vacuum is maintained. The gas separated from the sediment may proceed in the B direction, and components thereof may be analyzed.

The analysis method according to the present invention may further include analyzing a sulfur isotope in the residue. In more detail, the analyzing of the sulfur isotope is performed by another one of the above-described effects of the cadmium chloride which is a microbial activity inhibitor used in the present invention, that is, hydrogen sulfide ions ($HS^-$) present in the seawater meet the cadmium chloride to generate cadmium sulfide (CdS), and the cadmium sulfide may be extracted and precipitated since it is insoluble in water. Therefore, after only the cadmium sulfide is separated by separating the gas sample and filtering remaining residue, and the sulfur isotope is analyzed, thereby defining sulfur isotope fractionation between a sulfate and hydrogen sulfide due to sulfate reduction by microbial activity, and a sulfur cycle.

Hereinafter, the measurement method according to the present invention will be described in more detail with reference to the following Examples. Meanwhile, the following Examples are provided by way of example for explaining the present invention in more detail, and therefore, the present invention is not limited thereto.

Methods of measuring data and specification of devices described in the following Example are as follows.

(Methane Separator)

The methane separator including a stainless steel pipe having an outer diameter of 0.75 mm, and an inner diameter of 0.5 mm, and including a silicone tube having an inner diameter of 0.75 mm (thickness of 0.15 mm) and a length of 20 mm was used. The silicone tube was connected to the stainless steel pipe in a T-shaped vacuum housing in a vacuum state, and the stainless steel pipe was connected to a container containing a sample. In addition, Agilent GC 7890 was used to measure separated dissolved gas.

(Measurement of Concentration of Dissolved Gas)

1 ml of the separated gas obtained by passing the gas through the methane separator was injected into Agilent GC 7890 and component and content of the dissolved gas were analyzed. For analysis of components of hydrocarbon gas, capillary column (plot fused silica column: a length of 50 m, an inner diameter of 0.32 mm, a film thickness of 0.5 μm) was used, and a flame ionization detector (FID) was used as a detector. During the analysis of the hydrocarbon gas, a temperature of a GC inlet was set as 230° C., and a temperature of the detector was set as 250° C., and a temperature of an oven was maintained at 35° C. for 5 minutes and raised up to 195° C. at a rate of 20° C./min. For measurement of methane concentration, 1% of 10 ppm, 1% of 100 ppm, and 1% of 1000 ppm of gases were used as standard gases.

(Seawater)

Seawater was collected at each water depth at two vertices (Vertex 1: North latitude 35.4368, East longitude 129.5244, and Vertex 2: North latitude 35.6099, East longitude 129.5089) in the East Sea. Here, Niskin-rosette water sampler was used as the collector, and the collected seawater was stored by storing methods described in the following Examples and Comparative Examples.

Examples 1 to 10

At first, 1 ml of cadmium chloride ($CdCl_2$) was put into each brown bottle having a size of 20 ml, and then the brown bottle was sealed with a rubber stopper and an aluminum cap. In addition, air in the bottle was completely removed by using a vacuum pump so as to make the bottle in a vacuum state. Then, 3 ml of the seawater collected as described above was injected into the bottle by using a quantitative syringe, and the bottle was refrigerated at 4° C. until analysis was conducted.

Then, the container (bottle) was shaken at room temperature (25° C.) for about 5 minutes, and stored at a constant temperature and constant humidity bath at 25° C. for 48 hours, to achieve temperature equilibrium. In addition, after the sample was separated into dissolved gas and residue by using the methane separator, 1 ml of the separated dissolved gas was collected and analyzed by gas chromatography. Further, parts per million (ppmv) and micromole (μM) corresponding to 1/1000 of millimole (m mol) of measurement materials according to gas volume were shown in the following Table 1.

Comparative Examples 1 to 10

At first, 1 ml of mercury chloride (HgCl) was put into each brown bottle having a size of 125 ml and being made of the same materials as Examples 1 to 10, and then a magnetic bar was injected into the brown bottle. Then, the collected seawater was fully injected into the bottle, and the bottle was sealed with a rubber stopper and an aluminum cap and refrigerated at 4° C. until analysis was conducted.

In addition, 10 ml of the seawater was removed from the brown bottle by using a quantitative syringe so that a headspace is left, and mixed by using a magnetic stirrer at room temperature for 10 minutes. Further, 1 ml of gas was collected from the bottle by using the same methane separator as Examples and analyzed by gas chromatography. In addition, parts per million (ppmv) and a micromole (μM) corresponding to 1/1000 of millimole (m mol) of measurement materials according to gas volume were shown in the following Table 1. Equation 1 which converts ppm into a mol concentration is as follows.

$$CH_4 (\mu M) = [\chi M \times P_{atm} \times VH]/[R \times T \times f \times VS] \quad \text{[Equation 1]}$$

(VH=Volume of Brown Bottle, VS=Volume of Total Seawater Sample, χM=Mol Fraction of Methane, Patm=Pressure inside Bottle, R=Universal gas constant, T=Kelvin temperature inside Bottle, f=porosity (=1))

TABLE 1

| Vertex | Depth (meter below sea surface, nbss) | Example ppmv | μM | Comparative Example ppmv | μM |
|---|---|---|---|---|---|
| 1 | 5 | 3.8 | 0.268 | 1.0 | 0.003 |
| 1 | 40 | 11.9 | 1.113 | 0.1 | 0.000 |
| 1 | 60 | 11.9 | 1.126 | 0.5 | 0.002 |
| 1 | 80 | 8.9 | 0.843 | 0.2 | 0.001 |
| 1 | 95 | 8.2 | 0.777 | 0.5 | 0.002 |
| 2 | 5 | 6.6 | 0.612 | 0.7 | 0.002 |
| 2 | 35 | 4.1 | 0.373 | 7.0 | 0.022 |
| 2 | 40 | 8.3 | 0.759 | 5.4 | 0.017 |
| 2 | 45 | 8.0 | 0.740 | 4.6 | 0.015 |
| 2 | 47 | 5.4 | 0.491 | 7.1 | 0.023 |

As described above, it may be appreciated that in the method of measuring the dissolved methane in seawater according to the present invention, the recovery rate of the dissolved methane in the sample may be high even with the same amount of sample as compared to the existing measurement methods, and as a result, accuracy of an analysis may be increased. In addition, after the measurement is performed, cadmium sulfide may be extracted from the residue, such that the sulfur isotope analysis may be simultaneously conducted.

According to the method of measuring dissolved methane in seawater of the present invention as described above, the recovery rate of the dissolved methane may be maximally increased to improve an analysis rate accordingly, and the analysis of dissolved methane may be conducted even with a small amount of sample. In addition, with the method of measuring the dissolved methane in seawater according to the present invention, the sulfur isotope analysis in dissolved sulfurated water may be simultaneously conducted by using a sample from which the dissolved methane is extracted, in addition to the measurement of the dissolved methane.

What is claimed is:

1. A method of measuring dissolved methane in seawater, the method comprising:
  a) injecting a sample of seawater containing dissolved methane into a vacuum container containing a cadmium chloride solution injected thereinto and refrigerating the vacuum container;
  b) shaking the vacuum container, and achieving temperature equilibrium with an ambient temperature;
  c) separating the dissolved methane from residue by passing the sample in the vacuum container through a methane separator;
  d) analyzing the separated dissolved methane by a mass spectrometry, and
  e) filtering a precipitated material from the sample from which the dissolved methane is removed, and conducting a sulfur isotope analysis using a sample from which the dissolved methane is extracted.

2. The method of claim 1, wherein a) the injecting of the sample into the vacuum container includes:
- a1) injecting the cadmium chloride solution into the vacuum container and sealing the vacuum container;
- a2) making an inner part of the vacuum container to be in a vacuum state by using a vacuum pump; and
- a3) injecting the sample into the vacuum container and refrigerating the vacuum container at 0 to 10° C.

3. The method of claim 1, wherein the methane separator includes:
- a vacuum housing connected to the vacuum container, a mass spectrometer, and a residue processor;
- a silicone tube positioned in the vacuum housing, allowing the sample to pass through, and separating methane from the sample;
- a stainless steel pipe supplying the sample to the silicone tube; and
- a vacuum pump maintaining an inner part of the vacuum housing to be in a vacuum state.

4. The method of claim 3, wherein in the methane separator, the methane is separated by injecting the sample into the vacuum housing and then inserting the silicone tube attached to one end of the stainless steel pipe into the sample.

5. The method of claim 1, wherein the cadmium chloride solution is injected in an amount of 1 to 40 parts by weight based on 100 parts by weight of the sample.

\* \* \* \* \*